United States Patent
Kerselaers (10) Patent No.: US 10,661,082 B2
(45) Date of Patent: May 26, 2020

(54) NONINVASIVE INDUCTIVE BIOLOGICAL CONDITIONING DEVICE

(71) Applicant: NXP B.V., Eindhoven (NL)

(72) Inventor: Anthony Kerselaers, Herselt (BE)

(73) Assignee: NXP B.V., Eindhoven (NL)

( * ) Notice: Subject to any disclaimer, the term of this patent is extended or adjusted under 35 U.S.C. 154(b) by 264 days.

(21) Appl. No.: 15/799,146

(22) Filed: Oct. 31, 2017

(65) Prior Publication Data
US 2019/0126041 A1    May 2, 2019

(51) Int. Cl.
| | |
|---|---|
| A61N 2/02 | (2006.01) |
| A61N 1/36 | (2006.01) |
| A61N 1/40 | (2006.01) |
| A61N 1/04 | (2006.01) |
| A61N 2/00 | (2006.01) |

(52) U.S. Cl.
CPC ....... *A61N 1/36014* (2013.01); *A61N 1/0452* (2013.01); *A61N 1/0456* (2013.01); *A61N 1/0468* (2013.01); *A61N 1/3603* (2017.08); *A61N 1/36003* (2013.01); *A61N 1/36021* (2013.01); *A61N 1/40* (2013.01); *A61N 2/02* (2013.01); *A61N 2/006* (2013.01); *A61N 2/008* (2013.01)

(58) Field of Classification Search
CPC .................................................. A61N 2/00–12
See application file for complete search history.

(56) References Cited

U.S. PATENT DOCUMENTS

| | | | |
|---|---|---|---|
| 5,139,684 A | 8/1992 | Kaali | |
| 5,185,086 A | 2/1993 | Kaali | |
| 5,188,738 A | 2/1993 | Kaali | |
| 2003/0045770 A1 | 3/2003 | van Mullekom | |
| 2008/0306325 A1* | 12/2008 | Burnett | A61N 2/02 600/13 |
| 2013/0261711 A1* | 10/2013 | Sivo | A61N 1/40 607/103 |
| 2015/0335887 A1 | 11/2015 | Riddle et al. | |
| 2017/0113059 A1* | 4/2017 | Fisher | A61B 5/02405 |

FOREIGN PATENT DOCUMENTS

| | | |
|---|---|---|
| WO | WO-01/15774 A2 | 3/2001 |
| WO | WO-2009/073223 A1 | 6/2009 |
| WO | WO-2011/053607 A1 | 5/2011 |
| WO | WO-2015/142922 A1 | 9/2015 |

* cited by examiner

*Primary Examiner* — Thaddeus B Cox (57) ABSTRACT

One example discloses a noninvasive biological conditioning device, including: a first induction structure; a second induction structure; a barrier configured to block direct contact between the structures and a material; wherein the structures are configured to induce an electrical current in the material; and wherein the electrical current is configured to have a set of attributes for conditioning biological activity in the material.

20 Claims, 7 Drawing Sheets

NONINVASIVE INDUCTIVE BIOLOGICAL CONDITIONING DEVICE

The present specification relates to systems, methods, apparatuses, devices, articles of manufacture and instructions for biological conditioning.

SUMMARY

According to an example embodiment, a noninvasive biological conditioning device, comprising: a first induction structure; a second induction structure; a barrier configured to block direct contact between the structures and a material; wherein the structures are configured to induce an electrical current in the material; and wherein the electrical current is configured to have a set of attributes for conditioning biological activity in the material.

In another example embodiment, the electrical current is configured to attenuate the biological activity.

In another example embodiment, the electrical current is configured to is stimulate the biological activity.

In another example embodiment, the electrical current is only an AC electrical current.

In another example embodiment, the material is at least one of: a fluid, a biomaterial, water, blood, muscle, tissue, skin or a plant.

In another example embodiment, the barrier configured to galvanically block direct currents between the structures and the material.

In another example embodiment, the barrier is a dielectric.

In another example embodiment, the barrier is a set of biological cells.

In another example embodiment, the barrier is an air gap.

In another example embodiment, the material has a higher electrical conductivity than the barrier.

In another example embodiment, the biological activity includes at least one of: bacterial activity, viral activity, parasitic activity, or fungal activity.

In another example embodiment, the electrical current in the material is a first electrical current in a first material; the electrical current has a first set of electrical attributes configured to condition the first material; the induction structures are configured to further induce a second electrical current in a second material; the second electrical current has a second set of electrical attributes configured to condition the second material; and the first and second set of electrical attributes are different.

In another example embodiment, the electrical current in the material is a first electrical current; the induction structures are configured to induce a second electrical current for at least one of: pain reduction, brain stimulation, migraine reduction, muscle relaxation, wound care, joint motility increase, sleep quality improvement, or blood flow improvement; and the second current has an amplitude and/or frequency different from the first current.

In another example embodiment, further comprising a positioning circuit configured to generate a coupling factor between the first and second structures and the material; wherein the positioning circuit is configured to indicate when the first and second structures have a position for optimizing current generation in the material.

In another example embodiment, the positioning circuit is configured to inject a pilot signal into the material and which has a signal strength dependent upon the position of the device.

In another example embodiment, the pilot signal is the induced electrical current; the positioning circuit is configured to receive a signal from a magnetic sensor; and the signal from the magnetic sensor is based on the electrical current flowing in the material.

In another example embodiment, the positioning circuit is configured to sense an attribute generated by the material, and which has a signal strength dependent upon the position of the device.

In another example embodiment, the attribute is a heartbeat signal generated by a blood movement.

In another example embodiment, one of the inductive structures is part of an antenna circuit in at least one of: a wireless device, a RFID device, an NFMI device, an NFEMI device, or a Bluetooth device.

According to an example embodiment, a wearable device for noninvasive biological conditioning, the wearable comprising: a first induction structure; a second induction structure; a barrier configured to block direct contact between the structures and a material; wherein the structures are configured to induce an electrical current in the material; and wherein the electrical current is configured to have a set of attributes for conditioning biological activity in the material.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Bacteria, viruses, parasites and fungi entrained in the blood or other bodily fluids of a person or animal can be reduced using electric currents as described for example in issued U.S. Pat. No. 5,139,684.

Examples of such devices include routing the bodily fluids to an external device for treatment, or implanting a device in the person or animal for in-situ treatment.

Such devices require direct galvanic contact between the fluid and the device's electrodes (i.e. the electrodes are placed into the fluid) which can in some cases have negative effects (e.g. blood clotting leading to a stroke, further contamination of the fluid, secondary infections or inflammation).

Example embodiments of biological conditioning devices for inducing currents into biological materials (e.g. bodily fluids, tissues, or cells, either in vivo or in situ) are now presented. Such induction devices do not need to have direct galvanic contact with the materials to be conditioned (e.g. treated, altered, etc.), thereby reducing a chance of various negative effects, such as those mentioned above.

Such biological conditioning devices use magnetic fields to induce one or more electrical currents in one or more materials.

In some example embodiments multiple material and/or biological activities are targeted using a set of induced electrical currents, each having varied attributes that individually or constructively target each of the materials and/or biological activities in the materials.

Each induced electrical current is selected such that the targeted material and/or biological activity has a higher electrical conductivity compared to its surrounding materials and/or biological activities. Thus a higher induced current having a highest amplitude will flow in these targeted materials and/or biological activities.

Example embodiments of this device can be integrated into wearable products attached to the human or animal body or any other system (e.g. positioned around a wrist of a user).

In various example embodiments, the device may also be integrated with other functionality such as a wireless communication device. In such a combined device, the above described functionality can be activated by the user when required.

Also, in some example embodiments, antenna and other radiating structures currently used for communications (e.g. wireless, RFID, NFMI, NFEMI, Bluetooth, etc.) can be reused to induce the electrical currents in the materials.

Figure 1:
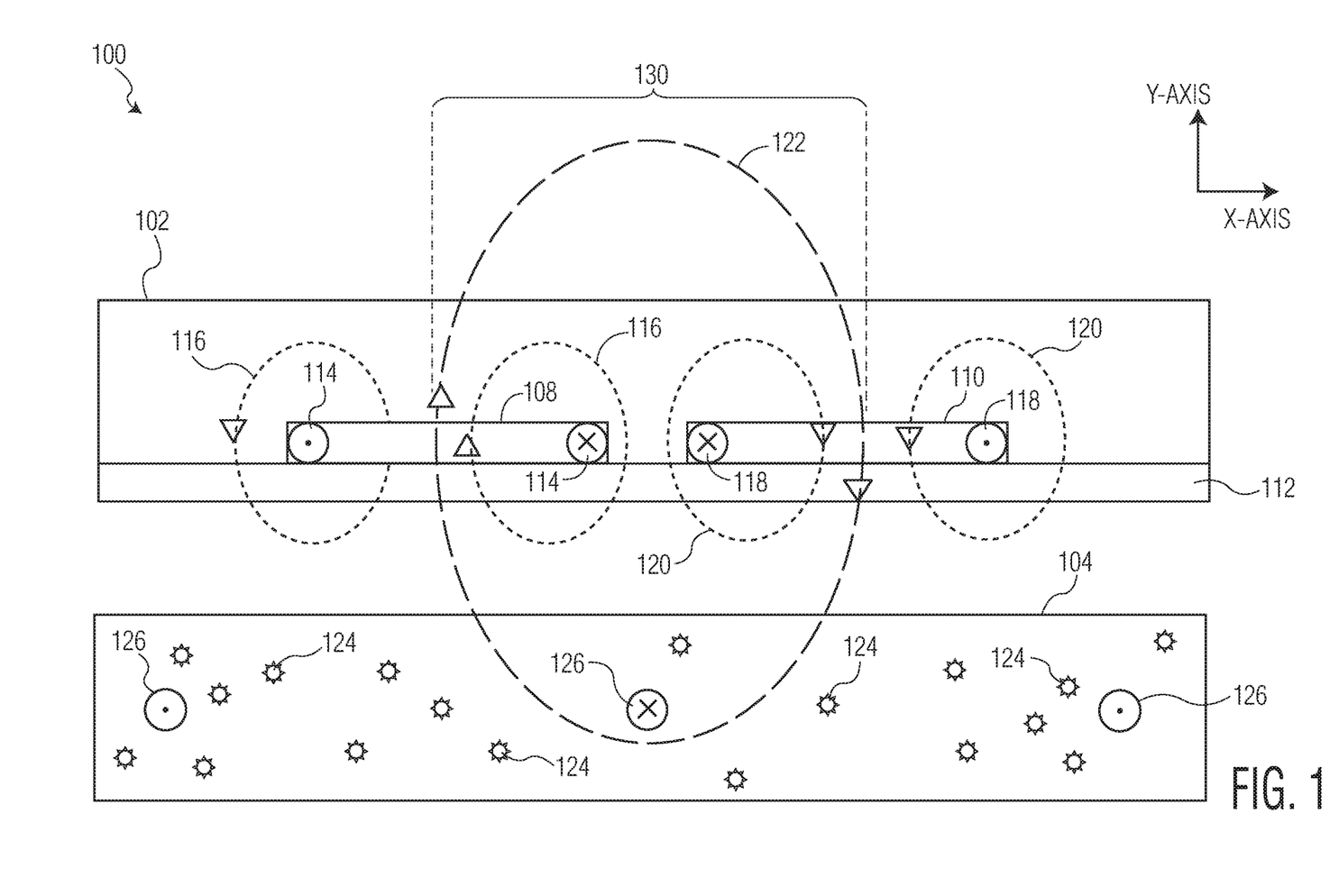
FIG. 1 is a first example of a noninvasive biological conditioning device.

FIG. 1 is a first example 100 of a noninvasive biological conditioning device 102. The first example 100 shows the noninvasive biological conditioning device 102 over a biomaterial 104.

The biological conditioning device 102 includes a first induction structure 108 and a second induction structure 110 separated by a distance 130.

In some example embodiments, one or more of the inductive structures 108, 110 is also part of another antenna circuit in or coupled to the device 102. This antenna could also be used for a wireless device, a RFID device, an NFMI device, an NFEMI device, or a Bluetooth device. The inductive structures 108, 110 can be planar or be conformed to a surface of the biomaterial 104. The inductive structures 108, 110 can also be embedded in a flexible substrate which also functions the internal barrier 112.

The device 102 also includes an internal barrier 112 or in some embodiments there is an external barrier, either of which blocks direct contact between the structures 108, 110 and the biomaterial 104. Thus the barrier 112 galvanically blocks direct currents from flowing between the structures and the biomaterial 104. The barrier 112 can be a dielectric, a set of biological cells, an air gap, a wearable's wrist band and so on. For the most efficient induction of electrical current 126 into the biomaterial 104, the biomaterial 104 should have a higher electrical conductivity than the barrier 112.

The first induction structure 108 includes a first coil wire 114 that when powered generates a first induction field 116. The second induction structure 110 includes a second coil wire 118 that when powered generates a second induction field 120.

The first and second fields 116, 120 together form a combined induction field 122. The fields 116, 120, 122 pass through the barrier 112 and induce the electrical current 126 in the bio material 104. In some example embodiments, the electrical current 126 is only an AC electrical current.

The biomaterial 104 for illustrative purposes is shown to include initial biological activity 124 being treated by the induced electrical current 126. The electrical current 126 is configured to have a set of attributes for conditioning biological activity in the bio material 104.

Instead of the biomaterial 104, other materials can be conditioned such as various fluids (e.g. water, blood, etc.) or tissues (e.g. human, animal, plant, muscle, skin, cells, etc.).

The biological activity includes at least one of: bacterial activity, viral activity, parasitic activity, or fungal activity.

In at least some example embodiments, the electrical current 126 is configured to attenuate the biological activity (e.g. reduction of bad bacteria) in the biomaterial 104. In other example embodiments, the electrical current 126 is configured to is stimulate the biological activity (e.g. promote growth of good bacteria) in the biomaterial 104.

In other embodiments, as discussed below, multiple currents are used. For example, the electrical current 126 in the material could be a first electrical current in a first material, and having a first set of electrical attributes configured to condition the first material. The induction structures 108, 100 are also configured to further induce a second electrical current in a second material, and having a second set of electrical attributes configured to condition the second material. The first and second set of electrical attributes would be different.

The inductive structures 108, 110 are shown from the side where currents in the first and second coil wires 114, 118 (e.g. windings) that are directed out of the FIG. 1 page are shown by a "dot" and currents that are directed into the page are shown by an "X". This same "dot" and "X" notation is used in FIG. 3C for magnetic field lines as well.

As mentioned, the first inductive structure 108 produces field lines 116 and the second inductive structure 110 produces field lines 120. A driving current (not shown) passed through the wires 114, 118 of the inductive structures 108, 110 by a power supply (see FIG. 5) are arranged such that the first induction field 116 and the second induction field 120 have an opposite polarity. The combined induction field 122 strength between the two inductive structures 108, 110 is thus lower than under both inductive structures 108, 110 due to this opposite polarity and more efficiently induces the electrical current 126 in the biomaterial 104.

Circuits (see FIG. 5) attached to the device 102 generate a signal shape, strength, frequency and duration for the combined induction field 122 that enhances the conditioning effects of the induced electrical current 126 in the biomaterial 104. Increased efficiency requires lower driving currents and thus lower power operation of the device 102 and related circuitry. Such lower power consumption enables the device 102 to be battery powered and have a small form factor and so could be included in a wearable device.

For adjusting the signal shape, strength, frequency and duration generated by the inductive structures 108, 110 resonance tuning circuits can be included such as one or more capacitor banks. Thus the structures 108, 110 can be configured to induce currents of various amplitudes, frequencies and wave shapes (e.g. a square wave) and optimized to have a maximum effect on a specific biological activity within the biomaterial 104. Multiple signals can also be generated from a same or multiple sets of structures 108, 110 and used to target multiple different biological activities in the biomaterial 104.

The induction fields 116, 120 in some example embodiments are defined by this equation:

$$Ei = \frac{\omega B r}{2}$$

Where:
Ei induced electrical field strength [V/m]
ω angular frequency [Hz]
B magnetic field [Tesla]
r loop area [m²]

The induced electrical current 126 is defined by this equation:

$$J = \sigma Ei$$

Where:
J current density [A/m²]
σ conductivity [Siemens/m]
Ei induced electrical field In some example embodiments and applications of the device 102, a minimum of 1 uA/mm2 is required for conditioning (e.g. altering/purifying) blood in a human.

To achieve induced electrical current 126 densities in the uA/mm2 range in some example embodiments, the first and second coil wires 114, 118 are excited by a first higher frequency to induce sufficient current amplitude and a second modulation frequency that can be lower, but still faster than a refresh rate of the biomaterial 104 (e.g. blood) being conditioned at the position of the wrist (in the order of 10 seconds).

In one example, a device 102 with two planar inductive structures 108, 110 on a flexible substrate using a 5 Volt drive voltage with a 10.6 MHz is the first frequency and 4 Hz is the second lower frequency results in induction fields 116, 120 of 1.4 µTesla and an induced electrical current 126 density in blood of 2.88 µA/mm².

The waveforms, amplitudes and frequencies required to induce currents in other biomaterials will be dependent on the material's respective conductivity.

Other biomaterials can be conditioned/altered. Example conductivities [Siemens/m] for various biomaterials at 10 MHz are as follows:

| | |
|---|---|
| skin | 0.2 |
| muscle | 0.62 |
| blood | 1.097 |

In some example embodiments, the electrical current's 126 effect in the biomaterial 104 additionally includes: pain reduction, brain stimulation, migraine reduction, muscle relaxation, wound care, joint motility increase, sleep quality improvement, and/or blood flow improvement.

Figure 2:
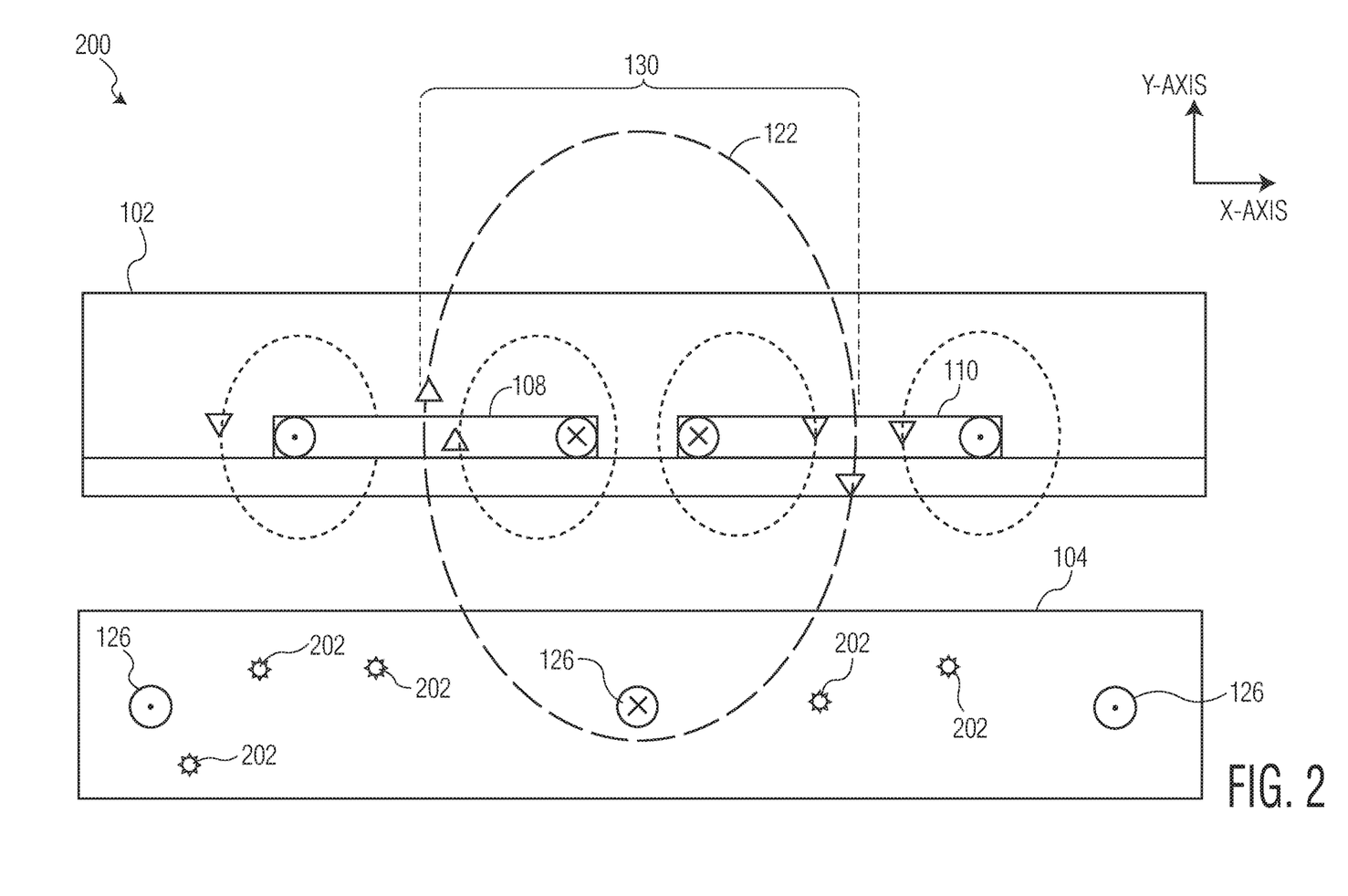
FIG. 2 is a second example of the noninvasive biological conditioning device.

FIG. 2 is a second example 200 of the noninvasive biological conditioning device 102. In the second example 200, the biomaterial 104 for illustrative purposes is shown to now include subsequent (i.e. attenuated/reduced) biological activity 202 after being treated by the induced electrical current 126.

Figure 3A:
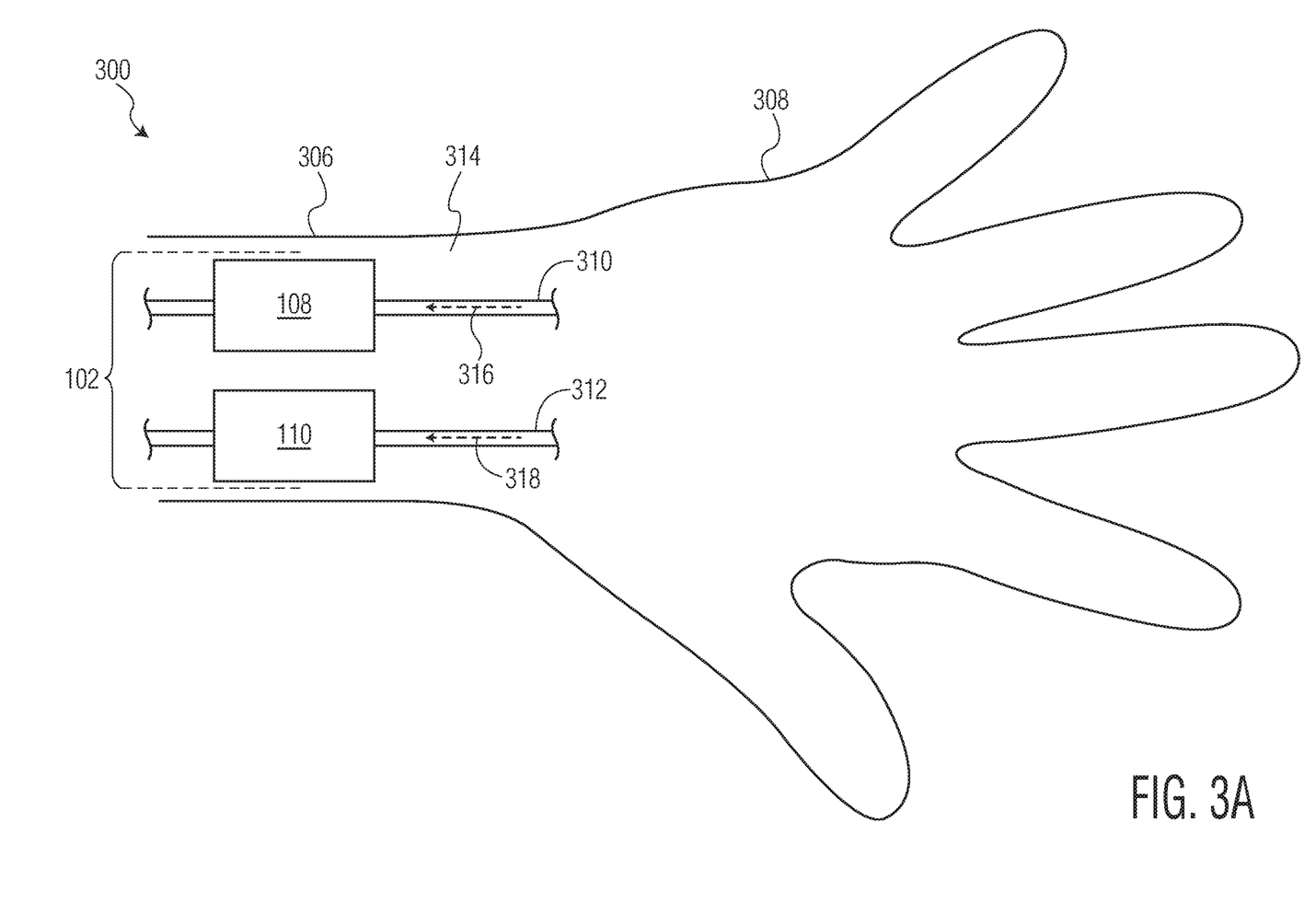
FIG. 3A is a first top view of a third example of the noninvasive biological conditioning device.

FIG. 3A is a first top view 300 of a third example of the noninvasive biological conditioning device 102. The first view 300 shows a wrist 306, a hand 308, a first blood vessel 310, a second blood vessel 312, an external barrier 314 (e.g. skin and muscle tissue), a first induced electrical current 316, and a second induced electrical current 318.

The inductive structures 108, 110 are positioned on the wrist 306 at a location ideally for a most efficient conditioning of blood in the blood vessels 310, 312.

Some example embodiments of the noninvasive biological conditioning device 102 include a positioning circuit (not shown) configured to generate a coupling factor (e.g. pulse strength, resonance frequency, minimum impedance, etc.) between the first and second structures 108, 110 and the biomaterial 104. The positioning circuit is configured to indicate when the first and second structures 108, 110 have a position for optimizing electrical current 126 generation in the biomaterial 104.

The induction structures 108, 110 can be optimally positioned using either active or passive techniques.

Example active techniques use the device 102 or another device to inject a pilot signal into the biomaterial 104 which is then optimized by moving the device 102.

Example passive techniques use the device 102 or another device to sense an attribute generated by the biomaterial 104, which is then optimized (e.g. for a maximum received signal strength) by moving the device 102.

One example of a passive technique involves sensing a heartbeat. For example the positioning circuit can detect a location of the structures 108, 110 where an amplitude of the heartbeat is largest with a heartbeat sensor, which would be at a maximum above a vein or artery.

One example of an active technique involves using a magnetic sensor (not shown). The magnetic sensor is positioned at a close but sufficient distance from the inductive structures 108, 110 which are located relatively nearby the veins or artery that is being targeted for conditioning. Since at least some current is induced in the targeted veins/artery that modest induced current will also generate a second magnetic field that is much smaller compared with the first and second magnetic induction fields 116, 120 generated by the structures 108, 110. This second magnetic field is largest when the induced electrical currents 316, 318 are largest. Thus the inductive structures 108, 110 can be moved until the amplitude of the second magnetic field becomes largest.

Figure 3B:
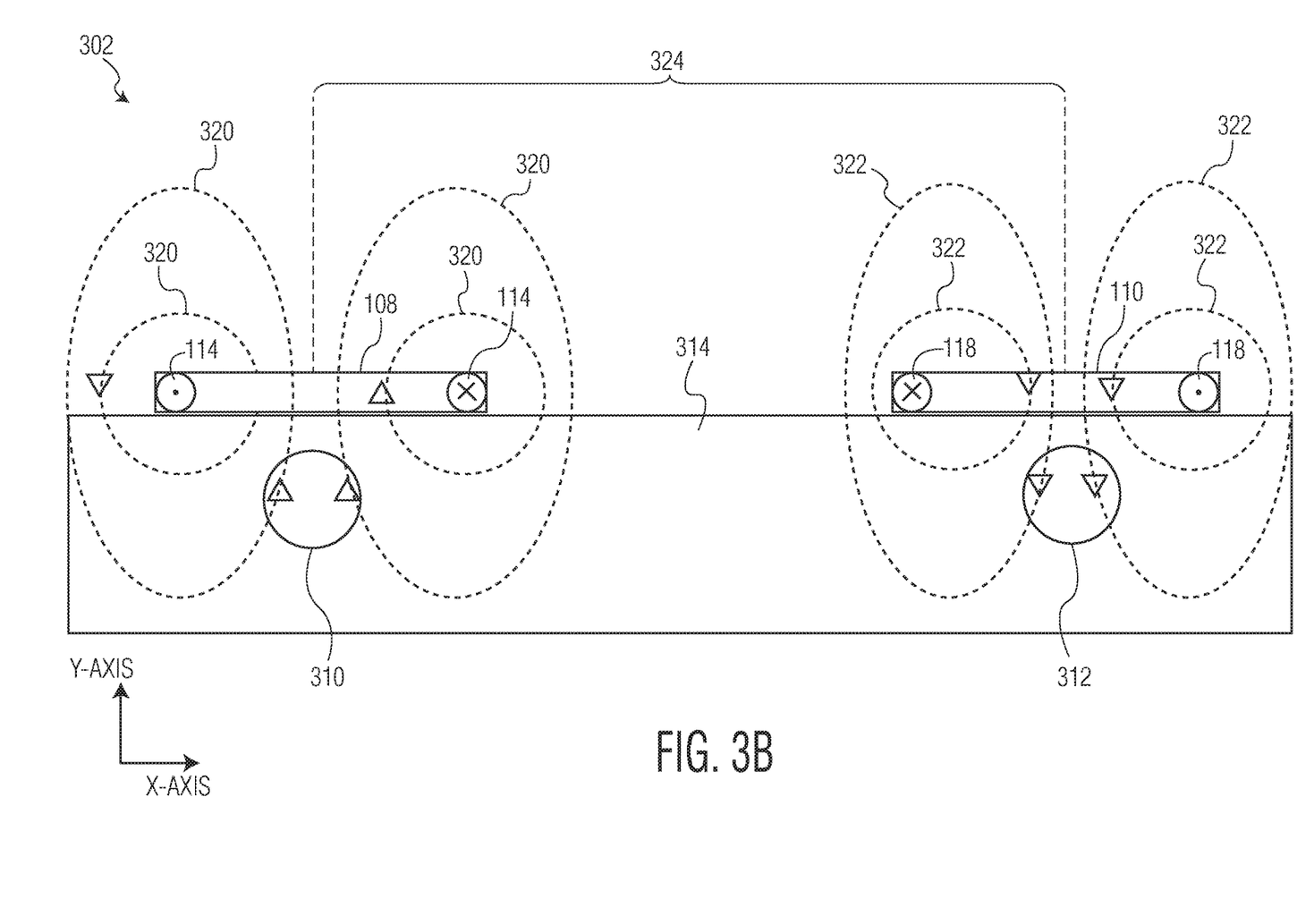
FIG. 3B is a cross-sectional view of the third example of the noninvasive biological conditioning device.

FIG. 3B is a cross-sectional view 302 of the third example of the noninvasive biological conditioning device 102. The cross-sectional view 302 shows a first induction field 320 generated by the first induction structure 108 and a second induction field 322 generated by the second induction structure 110.

The structures 108, 110 are separated by distance 324. The distance 324 reflects the optimized positioning of the structures 108, 110 over the first and second blood vessels 310, 312.

Figure 3C:
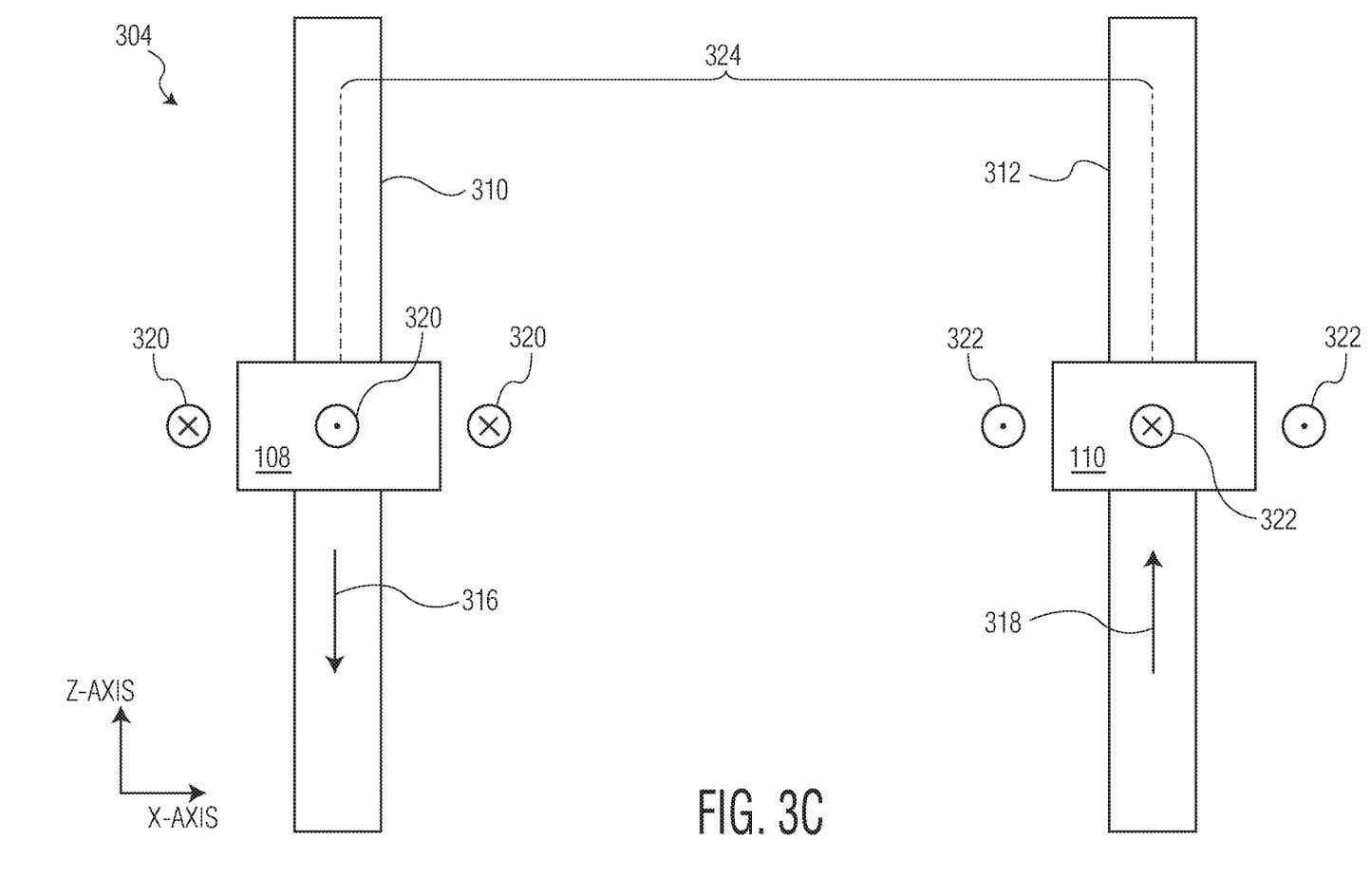
FIG. 3C is a second top view of the third example of the noninvasive biological conditioning device.

FIG. 3C is a second top view 304 of the third example of the noninvasive biological conditioning device 102. The second top view 304 also shows the first and second induced electrical currents 316, 318 flowing through the first and second blood vessels 310, 312.

Due to the different electrical properties (e.g. electrical conductivity) of the blood and wrist biomaterials, a higher current amplitude will be induced in the blood. The first and second induction fields 320, 322 are now shown using the "dot" and "X" notation discussed earlier.

Figure 4:
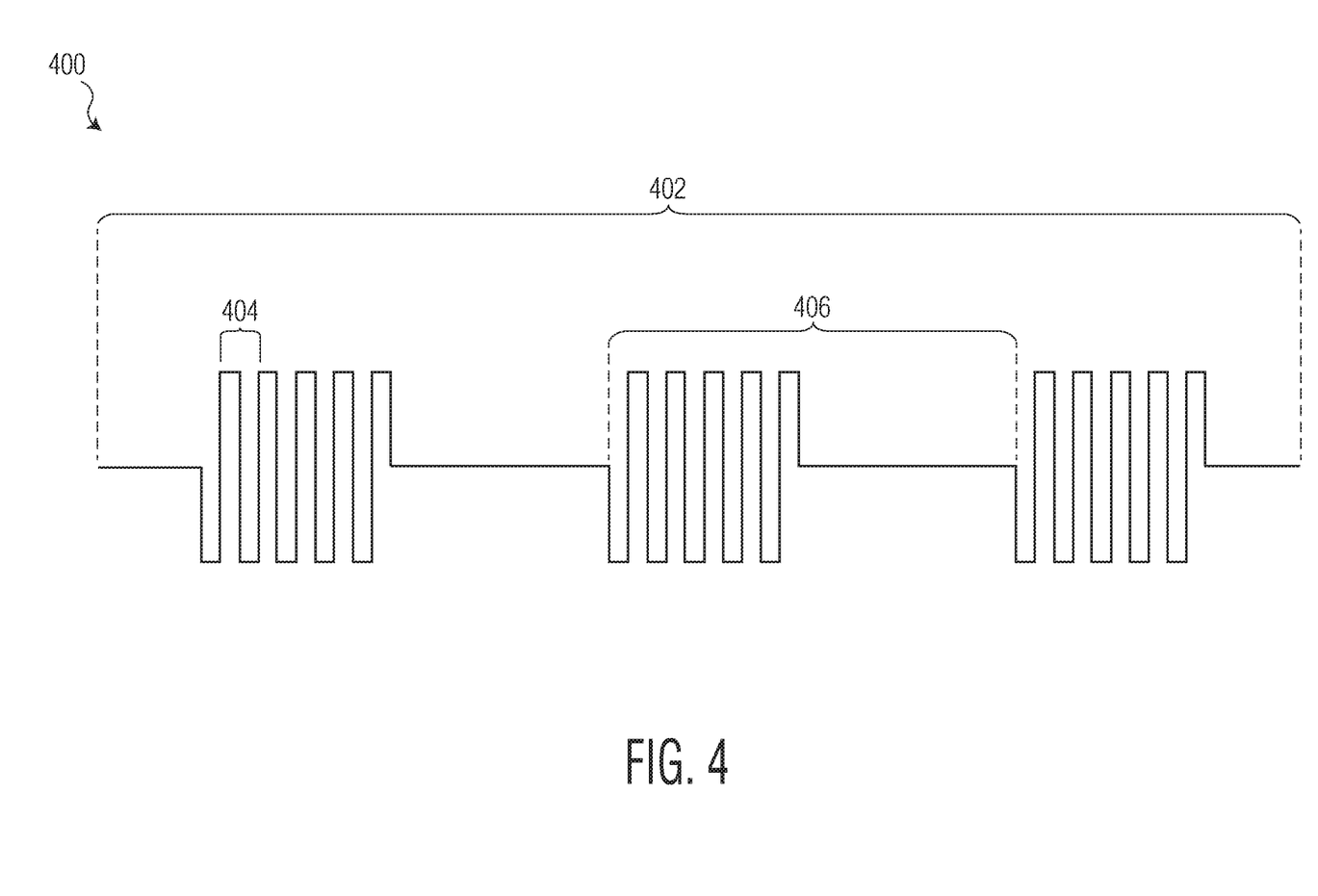
FIG. 4 is an example induction field and/or induced electrical current waveform generated by the noninvasive biological conditioning device.

FIG. 4 is an example 400 induction field and/or induced electrical current waveform 402 generated by the noninvasive biological conditioning device 102.

In this example the waveform uses square waves. A first higher frequency 404 is modulated by a second lower frequency 406. This example waveform 402 can be used in the example discussed above in FIG. 1 where the first higher frequency 404 is 10 MHz and the second lower frequency 406 is 4 Hz.

In some example applications of the device 102, this particular waveform 402 has a desired biological activity effect.

Figure 5:
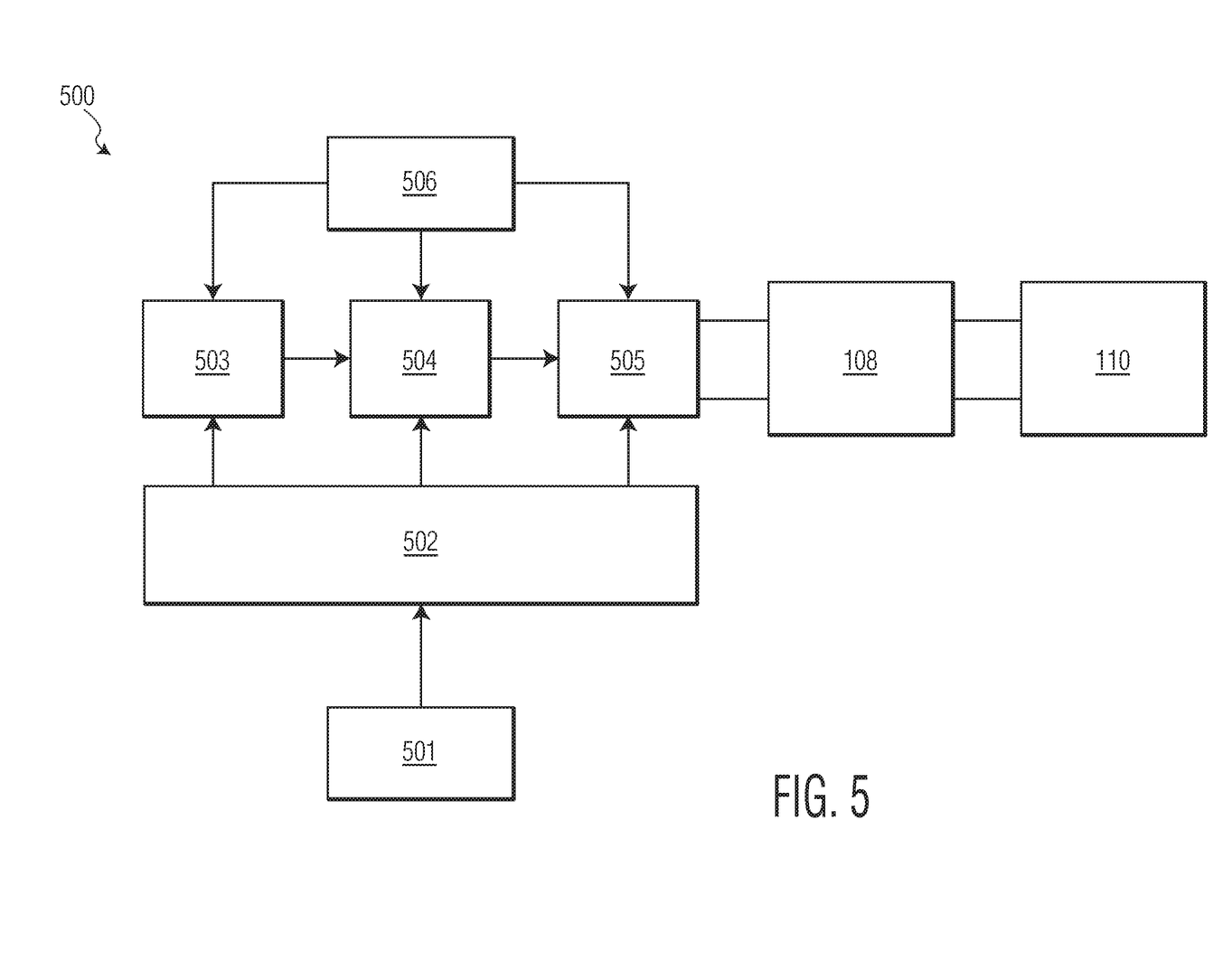
FIG. 5 is an example functional diagram of the noninvasive biological conditioning device.

FIG. 5 is an example functional diagram 500 of the noninvasive biological conditioning device 102. The user interface 501 controls the device. Processor 502 can steer the different functional blocks. The first signal with a first frequency and shape, is generated by the oscillator 503. The first signal is modulated in the modulator 504 by a second signal with a second frequency and shape.

The driver 505 provides the required driving current to the first induction structure 108 (e.g. first coil) and the second induction structure 110 (e.g. second coil). These different electronic blocks are supplied power by the supply section 506, containing a battery and a charging circuitry. The charging circuitry may be supplied by an external wired line, like a USB line or may have a wireless charging functionality.

Various instructions and/or operational steps discussed in the above Figures can be executed in any order, unless a specific order is explicitly stated. Also, those skilled in the art will recognize that while some example sets of instructions/steps have been discussed, the material in this specification can be combined in a variety of ways to yield other examples as well, and are to be understood within a context provided by this detailed description.

In some example embodiments these instructions/steps are implemented as functional and software instructions. In other embodiments, the instructions can be implemented either using logic gates, application specific chips, firmware, as well as other hardware forms.

When the instructions are embodied as a set of executable instructions in a non-transient computer-readable or computer-usable media which are effected on a computer or machine programmed with and controlled by said executable instructions. Said instructions are loaded for execution on a processor (such as one or more CPUs). Said processor includes microprocessors, microcontrollers, processor modules or subsystems (including one or more microprocessors or microcontrollers), or other control or computing devices. A processor can refer to a single component or to plural components. Said computer-readable or computer-usable storage medium or media is (are) considered to be part of an article (or article of manufacture). An article or article of manufacture can refer to any manufactured single component or multiple components. The non-transient machine or computer-usable media or mediums as defined herein excludes signals, but such media or mediums may be capable of receiving and processing information from signals and/or other transient mediums.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A noninvasive biological conditioning device, comprising:
   a first induction structure;
   a second induction structure;
   a barrier configured to block direct contact between the structures and a material;
   wherein the structures are configured to induce an electrical current in the material;
   wherein the electrical current is configured to have a set of attributes for conditioning biological activity in the material; and
   wherein at least one of the induction structures is also part of an antenna configured to wirelessly communicate with other devices.

2. The device of claim 1:
   wherein the electrical current is configured to attenuate the biological activity.

3. The device of claim 1:
   wherein the electrical current is configured to stimulate the biological activity.

4. The device of claim 1:
   wherein the electrical current is only an AC electrical current.

5. The device of claim 1:
wherein the material is at least one of: a fluid, a biomaterial, water, blood, muscle, tissue, skin or a plant.

6. The device of claim 1:
wherein the barrier is configured to galvanically block direct currents between the structures and the material.

7. The device of claim 1:
wherein the barrier is a dielectric.

8. The device of claim 1:
wherein the barrier is a set of biological cells.

9. The device of claim 1:
wherein the barrier is an air gap.

10. The device of claim 1:
wherein the material has a higher electrical conductivity than the barrier.

11. The device of claim 1:
wherein the biological activity includes at least one of: bacterial activity, viral activity, parasitic activity, or fungal activity.

12. The device of claim 1:
wherein the electrical current in the material is a first electrical current in a first material;
wherein the electrical current has a first set of electrical attributes configured to condition the first material;
wherein the induction structures are configured to further induce a second electrical current in a second material;
wherein the second electrical current has a second set of electrical attributes configured to condition the second material; and
wherein the first and second set of electrical attributes are different.

13. The device of claim 1:
wherein the electrical current in the material is a first electrical current;
wherein the induction structures are configured to induce a second electrical current for at least one of: pain reduction, brain stimulation, migraine reduction, muscle relaxation, wound care, joint motility increase, sleep quality improvement, or blood flow improvement; and
wherein the second current has an amplitude and/or frequency different from the first current.

14. The device of claim 1:
further comprising a positioning circuit configured to generate a coupling factor between the first and second structures and the material;
wherein the positioning circuit is configured to indicate when the first and second structures have a position for optimizing current generation in the material.

15. The device of claim 14:
wherein the positioning circuit is configured to inject a pilot signal into the material and which has a signal strength dependent upon the position of the device.

16. The device of claim 15:
wherein the pilot signal is the induced electrical current;
wherein the positioning circuit is configured to receive a signal from a magnetic sensor; and
wherein the signal from the magnetic sensor is based on the electrical current flowing in the material.

17. The device of claim 14:
wherein the positioning circuit is configured to sense an attribute generated by the material, and which has a signal strength dependent upon the position of the device.

18. The device of claim 17:
wherein the attribute is a heartbeat signal generated by a blood movement.

19. A wearable device for noninvasive biological conditioning, the wearable device comprising:
a first induction structure;
a second induction structure;
a barrier configured to block direct contact between the structures and a material;
wherein the structures are configured to induce an electrical current in the material; and
wherein the electrical current is configured to have a set of attributes for conditioning biological activity in the material; and
wherein at least one of the induction structures is also part of an antenna configured to wirelessly communicate with other devices.

20. A noninvasive biological conditioning device, comprising:
a first induction structure;
a second induction structure;
a barrier configured to block direct contact between the structures and a material;
wherein the structures are configured to induce an electrical current in the material; and
wherein the electrical current is configured to have a set of attributes for conditioning biological activity in the material; and
wherein at least one of the induction structures is also part of a near-field antenna configured to wirelessly communicate with other devices.

* * * * *